United States Patent [19]

Holland

[11] Patent Number: 4,702,111
[45] Date of Patent: Oct. 27, 1987

[54] SONIC WOOD TESTING APPARATUS AND METHOD

[75] Inventor: John F. Holland, Lansing, Mich.

[73] Assignee: American Energy Services, Inc., Richmond, Mich.

[21] Appl. No.: 851,499

[22] Filed: Apr. 1, 1986

[51] Int. Cl.$^4$ ............................................. G01N 29/04
[52] U.S. Cl. ........................................ 73/579; 73/602
[58] Field of Search ................................. 73/579, 602

[56] References Cited

U.S. PATENT DOCUMENTS

| 2,418,284 | 4/1947 | Winchel et al. | |
|---|---|---|---|
| 2,549,076 | 4/1951 | Gallagher et al. | |
| 2,946,217 | 7/1960 | Fruengel | |
| 3,291,143 | 12/1966 | Russell | |
| 3,345,861 | 10/1967 | Heath | 73/597 |
| 3,361,225 | 1/1968 | Nichols | |
| 3,531,983 | 10/1970 | Heath et al. | 73/597 |
| 3,580,056 | 5/1971 | Warner | 73/579 |
| 3,877,294 | 4/1975 | Shaw | 73/579 |
| 4,059,988 | 11/1977 | Shaw | 73/579 |
| 4,342,229 | 8/1982 | Massa | 73/579 |
| 4,399,701 | 8/1983 | Dunlop | 73/579 |
| 4,400,980 | 8/1983 | Lepert | 73/579 |
| 4,479,386 | 10/1984 | Beggs et al. | 73/579 |
| 4,502,329 | 3/1985 | Fukunaga et al. | 73/579 |
| 4,519,245 | 5/1985 | Evans | 73/579 |

FOREIGN PATENT DOCUMENTS 1297213 5/1962 France .
156338 3/1962 U.S.S.R. .

OTHER PUBLICATIONS

Article entitled "Extending Wood Pole Life" by William C. Hayes, Electrical World, Feb. 1986, pp. 41–47.

Primary Examiner—Howard A. Birmiel
Attorney, Agent, or Firm—Harness, Dickey & Pierce

[57] ABSTRACT

An improved non-destructive sonic testing apparatus is disclosed which is specially adapted for use in assessing the integrity of wooden utility poles. In one embodiment, the sonic testing apparatus of the present invention operates to perform a Fourier analysis on a signal which has been transmitted through a pole to be tested. Two or more criteria selected from the group of mode, mean, median and range are then determined for the resulting waveform and compared in order to provide a visual display representative of the condition of the pole being tested. In another embodiment of the present invention a software peak seeking algorithm is utilized to provide an envelope waveform from which successive half lives are determined. The relative time duration for successive half lives are compared to provide an indication of the amount of decay.

9 Claims, 8 Drawing Figures

SONIC WOOD TESTING APPARATUS AND METHOD

BACKGROUND AND SUMMARY OF THE INVENTION

The present invention relates generally to sonic testing apparatus and more specifically to such sonic testing apparatus which is specifically adapted for testing of wooden structural members and in particular wooden utility poles.

Vast numbers of wooden poles are in use today by the utilities in order to support various power transmission and communication wires in elevated relationship to the ground. While generally these wooden poles are subjected to various chemical treatments in order to increase the longevity thereof, they nevertheless are subject to decay which may vary greatly in the rate thereof dependent upon various environmental conditions such as soil composition, moisture, and the like. Accordingly, because of the potential hazards created by an excessively decayed utility pole, the public utilities and others utilizing such poles have found it necessary to develop testing procedures in order to ascertain when the amount of decay present within the pole has reached such a magnitude as to require replacement thereof. Because the cost of purchasing and installing utility poles is relatively high, it is desirable to maximize the useful life of each and every pole. However, because of the widely varying rates of decay which may change dramatically from one pole to the next in the same pole line, it is not possible to merely perform representative testing. Further compounding the difficulty of obtaining reliable and accurate information as to the integrity of the wooden pole is the fact that a majority of the decay which may be present in a given pole will be hidden well within the interior thereof and not be readily discernible from a mere visual inspection thereof. Also, the most prevalent areas for such decay to occur are centered about the ground level contact with the pole. Typically, excessive decay will not occur well below ground level due to the lack of oxygen which is a necessary element for the decomposition of the wood fibers. Similarly, decay will rarely occur much above ground level due to the lack of significant moisture concentrations over extended periods of time as in this area the pole is openly exposed to the drying effects of the surrounding atmosphere.

In developing testing procedures and apparatus for use in conjunction with the testing of such wooden utility poles, it is extremely desirable to provide apparatus which is capable of operating substantially independently of the skill of the operator so as to avoid significant variation in the accuracy of such tests between different operators. Further, it is desirable to provide apparatus which is portable and which may be easily operated with a minimum of pre-test preparation therefor. It is also important because of the area within which most decay of such wooden poles occurs that the test apparatus be capable of covering a relatively large vertical spectrum of the pole in a signle test so as to avoid the necessity of excavating the ground around the pole as well as to avoid the need to conduct successive tests at different elevations thereon. Another important factor for consideration is that a variety of different species of trees may be utilized for such utility poles and these species may very well be intermixed along the same pole line. Thus, it is important that the test apparatus be capable of readily accommodating a wide variety of different wood species which may have different sonic transmission characteristics without the need to invest the time and effort for recalibrating of the test apparatus.

The present invention provides significantly improved sonic testing apparatus which greatly overcomes the difficulties and problems of apparatus heretofore developed. The sonic testing apparatus of the present invention is designed to substantially eliminate the possibility of operator error and may be packaged in such a manner as to render it easily portable. Further, the apparatus is easy and convenient to use and does not require any excavation work to be performed in the vicinity of the pole in order to ascertain the condition of the pole over the entire area of likely decay. Because the apparatus is capable of rendering consistent test results from operator to operator, the number of erroneous or questionable bad pole readings will be greatly reduced thereby significantly decreasing the number of visual boring operations which must be performed. These factors thus all contribute to substantial reduction in the overall costs associated with performing integrity tests on such wooden poles.

It should be noted, however, that while the present disclosure is specifically directed to the use of the present invention in connection with the integrity testing of wooden utility poles, the sonic testing apparatus of the present invention is also well suited for use in non-destructive testing of virtually any wooden structural members such as for example wooden bridge members or the like. Of course, when the testing apparatus is to be utilized in connection with testing of milled timbers or the like, it will be necessary to ascertain the character of the cut resulting in the timber. That is to say, that whether the timber is center cut, quarter-sawn, etc. may very well affect its sonic transmission capabilities and thus necessitate ascertaining the type of cut resulting in formation of the timber. However, given appropriate reference information and test object information, the principals employed in the present invention as utilized in connection with the testing of wooden utility poles is believed to be equally applicable to these other types of structural wooden members.

Additional advantages and features of the present invention will become apparent from the subsequent description and the appended claims taken in conjunction with the accompanying drawings.

DESCRIPTION OF THE PREFERRED EMBODIMENTS

Figure 1:
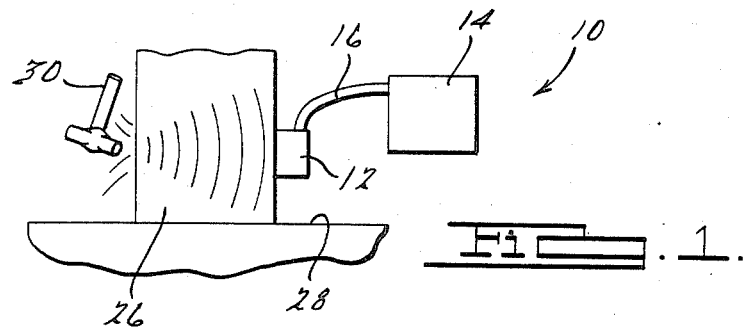
FIG. 1 is a schematic illustration of a sonic testing apparatus in accordance with the present invention shown in operative relationship to a wooden utility pole to be tested.
Figure 2:
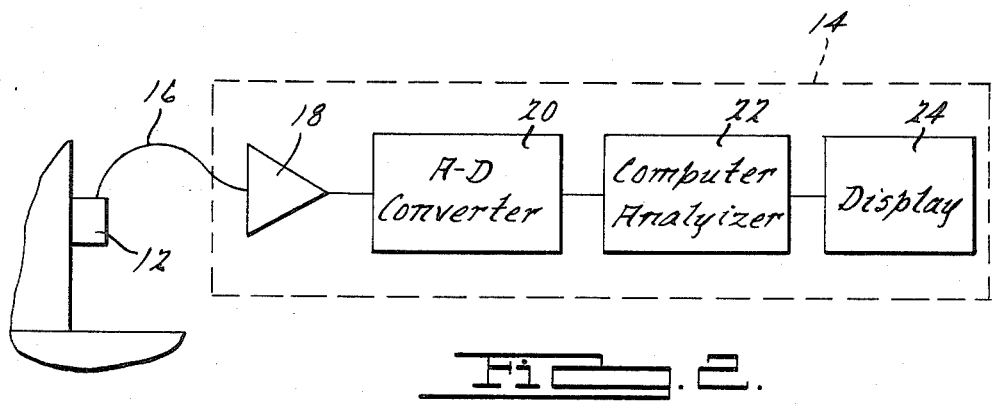
FIG. 2 is a schematic block diagram of the sonic testing apparatus in accordance with the present invention.

Referring now to the drawings and more particularly to FIGS. 1 and 2, there is illustrated in schematic form a first embodiment of the present invention indicated generally at 10. The sonic pole tester 10 of the present invention includes a transducer 12 interconnected to a central processing assembly 14 by means of suitable conductors 16.

Central processing assembly 14 contains an operational amplifier 18 operative to receive the electrical signal provided by transducer 12, to amplify same and supply this thus amplified signal to an analog to digital converter 20. The thus digitized signal is then supplied to a computer analyzer 22 for further processing. The computer is programmed to perform a Fourier transform analysis of the digitized signal and to generate an array representative of the relationship between the frequency and energy of the signal received and transmitted by transducer 12. Further, analysis of the resulting array is then performed by the computer 22 so as to determine at least two criteria selected from the group of range, median, mean, or mode for the resulting waveform. From the relative relationship of the two selected criteria, the computer will generate a signal indicative of the acceptability or nonacceptability of the article being tested which will be fed to a visual display device 24.

More specifically, as previously mentioned, sonic testing 10 is specifically designed and intended to be used in the evaluation of the soundness of wooden utility poles while in service. In order to utilize the sonic testing apparatus 20 of the present invention for this purpose, the transducer 12 is positioned in contact with the pole 26 to be tested immediately adjacent or slightly above ground level 28. It should be noted that the elimination of any need to position the transducer 12 below ground level (where a large potential for decay exists) as has previously been required with other types of testing apparatus represents a significant advantage in terms of ease of use as well as the time required to properly perform the tests.

Figure 3:
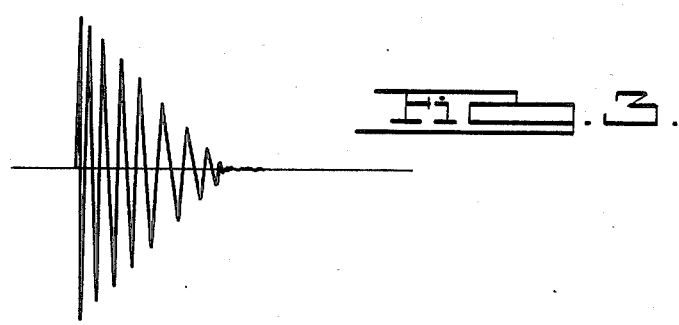
FIG. 3 is a graphical illustration of a sensed sonic signal transmitted through a utility pole having little or no decay therein.
Figure 4:
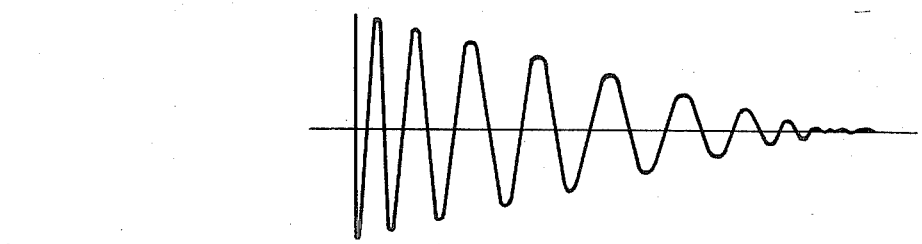
FIG. 4 is a graphic representation similar to that of FIG. 3 but indicating a sonic signal which has been transmitted through a wooden utility pole having an extensive amount of decay therein.

With the central processing unit 14 energized preferably by means of a suitable portable power source preferably located internally thereof and the transducer in position, the opposite side of the pole to be tested is impacted by means of a suitable tool such as a conventional hammer 30. This impact will generate a sonic signal within the pole which will be transmitted through the wood fibers comprising same and be received as an analog signal by the transducer 12. For any given impact force, the resulting signal will vary in terms of the frequency of response, the amplitude of the signal, and the time duration over which the signal is received. These factors are dependent upon a wide variety of variables including the species of the wood being tested, the amount of decay which has taken place and the size of the pole. FIGS. 3 and 4 show representative signals which may be received and transmitted by the transducer when good and bad wood is encountered. As is illustrated, the frequency and amplitude of the signal in FIG. 4 (indicative of substantial decay) are significantly less than that of the signal in FIG. 3 whereas the time duration of the signal in FIG. 4 is substantially greater than that of FIG. 3. The present apparatus is capable of overcoming the difficulties of dealing with this wide variety of variables and provides an accurate indication of the condition of the pole being tested.

Figure 5:
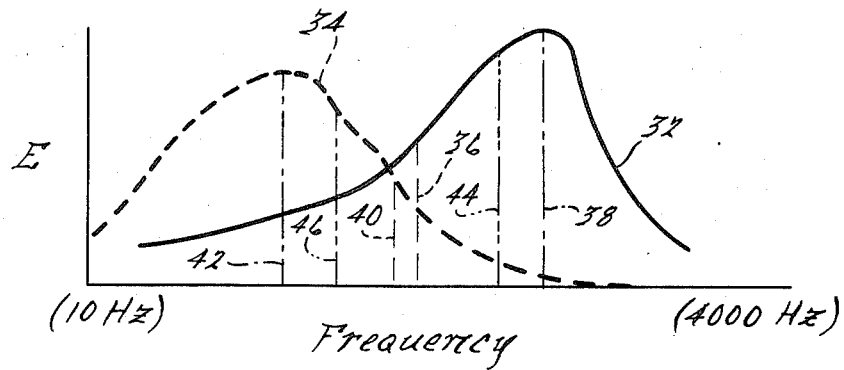
FIG. 5 is a graphical illustration of the resulting computer analysis performed on the signal transmitted through the wood pole.

The signal thus received by transducer 12 is thereafter transmitted to the central processing unit 14 and particularly to the operational amplifier whereafter the amplified signal is digitized by means of the analog to digital converter 20. As mentioned above, the digitized signal is then subject to a Fourier transform analysis by computer 22, the result of which will be an output showing the amount of energy contained within the signal over the range of frequency received by the transducer. FIG. 5 shows representative plots of this signal, line 32 being representative for the signal illustrated in FIG. 3 (good wood) and line 34 thereof being generally representative of the signal illustrated in FIG. 4 (substantial decay).

Next, computer 22 will analyze the results of this Fourier transform and determine any two of the mean, mode, median and range for the resulting plot. From a comparison of the two selected criteria, the computer will then provide via display 24 a visual indication of the condition of the pole being tested.

More specifically, let us assume the two criteria selected for comparison are mean and mode. As shown in FIG. 4, the mean or arithmetic average energy level is represented by line 36 and occurs at a frequency substantially below the frequency of the mode or peak energy level represented by line 38 for plot 32 and thus indicates that a greater amount of the energy transmitted through the pole was at a relatively high frequency and thus little, if any, decay has occurred. Conversely, with respect to plot 34, it is noted that the mean represented by line 40 occurs at a frequency substantially above the frequency of the mode represented by line 42. Thus, this tells us that a greater amount of energy transmitted through the pole was at the lower end of the frequency range and hence signifies substantial decay within the pole being tested.

A similar relationship is established if the two criteria selected for analysis are the mean and median. As shown in FIG. 5, for good wood (plot 32) the median represented by line 44 occurs at a higher frequency than the mean whereas for bad wood (plot 32) the median represented by line 46 occurs at a frequency below that of the mean (line 40).

If the selected criteria are range and any one of mean, median or mode, the approach will be to identify the midpoint of the frequency range for the signal and compare the relative relationship therebetween. If the selected criteria or mean, mode or median occurs at a frequency above the midpoint of the frequency range, the wood is good whereas if it falls below the midpoint, substantial decay has occurred.

Lastly, if the two selected criteria are the mode and median, it is illustrated in FIG. 5, that for good wood (plot 32) the mode 38 will occur at a higher frequency than the median 44 whereas the relationship is reversed for bad wood (plot 34).

It should be noted that because the present invention is based on the relative frequency at which the various criteria selected occur relative to each other rather than on any absolute criteria, the need to recalibrate or otherwise adjust the test apparatus so as to compensate for the different characteristics of species of wood is effectively eliminated. Further, it should also be noted that the force of the impact to which the pole is subjected will not alter the accuracy of the test results as long as a sufficient minimum impact force is applied and it is not so excessive as to exceed the level of saturation both of which condition extremes may be monitored automatically by the apparatus. Thus, the present invention effectively removes a substantial amount of the dependency on the abilities of the operator to achieve accurate test results and also facilitates rapid and relatively easy performance of the tests.

Figure 6:
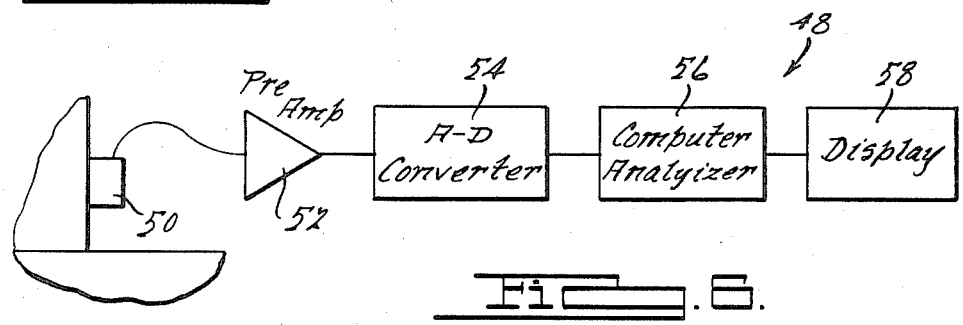
FIG. 6 is a schematic block diagram of another embodiment of sonic testing apparatus in accordance with the present invention.
Figure 7:
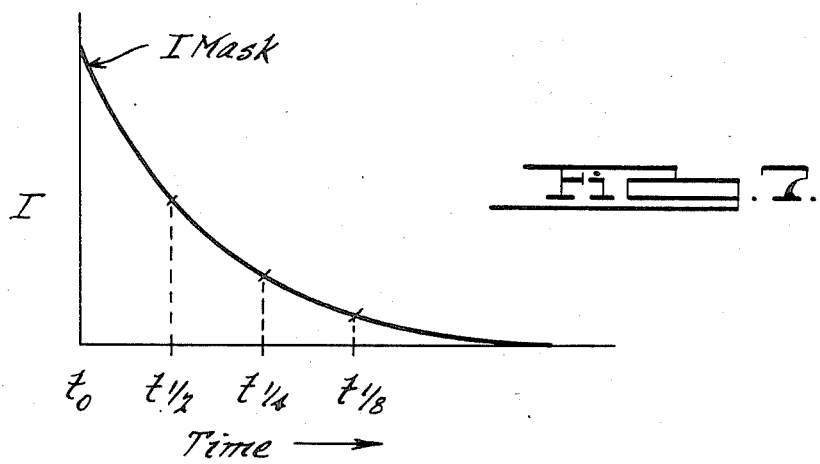
FIG. 7 is a graphical illustration of the computer analysis performed on the sensed sonic signal by the apparatus of FIG. 6 wherein the sonic signal has been transmitted by wood having little or no decay.
Figure 8:
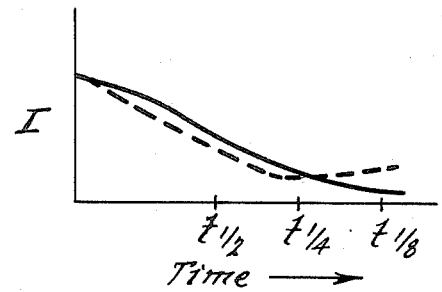
FIG. 8 is a graphical illustration of a signal similar to that of FIG. 7 however, in this case the sonic signal has been transmitted through wood having a substantial amount of decay.

Another embodiment of the present invention is illustrated and will be described with reference to FIGS. 6 through 8. In this embodiment, sonic testing apparatus 48 comprises a transducer 50 operative to supply a sensed signal to a preamplifier 52 after which the signal is digitized by an analog to digital converter 54. The resulting digitized signal is then supplied to a computer analysis unit 56 for analysis and generation of a resulting output display via display device 58 indicative of the test results.

In this embodiment, the preamplifier 52 includes a full wave rectifier, the output of which is then supplied to the analog to digital converter 54 and thence to the computer. The computer analyzer will then process this signal to identify peak values so as to establish an envelope for the signal sensed by transducer 50. The resulting envelope signal may be graphically represented by FIGS. 7 and 8 which show representative signals for good wood and bad wood, respectively.

The computer analyzer then processes this signal to determine the length of time required for the value of the envelope to drop to one half of its initial value or the half life of the signal. As illustrated in FIG. 7 at time $t_{\frac{1}{2}}$, the value I of the signal will be equal to one half the value at $t_0$ and similarly at $t_{\frac{1}{4}}$, the value I will be one half the value at $t_{\frac{1}{2}}$. Preferably, three such half lives will be determined for a given signal. The time required for the half life will then provide an indication of the condition of the wood being tested. As noted previosuly, good wood results in a faster and higher frequency transmission of sonic impulses whereas bad wood results in slower and lower frequency transmission. Thus, a short half life will be indicative of good wood whereas a long half life will be indicative of bad wood. It should be noted that a comparison of the relative lengths of time for each of the successive half lives may also be made to further verify the accuracy of the test and hence condition of the wood. With respect to good wood, it has been found that the successive half lives will require shorter time whereas with bad or substantially decayed wood, the successive half lives will require a greater time interval.

It should be noted, however, that this embodiment of the present invention does not render test results which are totally independent of the characteristics of wood species as harder woods will have shorter half lives than softer woods even with no decay present. Hence, it may be necessary to recalibrate the apparatus should woods of dramatically differing hardness be tested. Nevertheless, because the vast majority of wood poles which are to be tested will be of species having relatively closely related hardness and frequency transmission characteristics, it is not believed a significant amount of recalibration would be required.

Wile it will be apparent that the preferred embodiments of the invention disclosed are well calculated to provide the advantages and features above stated, it will be appreciated that the invention is susceptible to modification, variation and change without departing from the proper scope or fair meaning of the subjoined claims.

I claim:

1. A non-destructive sonic testing apparatus for ascertaining the integrity of wooden members comprising:
   means for receiving sonic energy imparted to said wooden member and generating a signal in response to said received sonic energy;
   analyzing means for receiving said signal and performing an analysis thereon to determine energy levels as a function of frequency for said signal, said analyzing means also being operative to determine at least two criteria selected from the group comprising the mean, mode, median and range for said energy levels as a function of frequency and to determine the relative relationship between said two criteria; and
   means responsive to the relative relationship between said two criteria to provide a visual indication representative of the condition of said wooden member.

2. A testing apparatus as set forth in claim 1 wherein said analyzing means perform a Fourier transform analysis on said signal.

3. A testing apparatus as set forth in claim 1 wherein said two criteria are mean and mode.

4. A testing apparatus as set forth in claim 3 wherein said visual indication of the condition of said wooden member shows substantial decay when said mean occurs at a frequency higher than said mode.

5. A testing apparatus as set forth in claim 1 wherein said relative relationship comprises a determination of the relative frequency levels at which said at least two criteria occur.

6. A non-destructive sonic testing apparatus for ascertaining the integrity of wooden members comprising:
   means for receiving sonic energy imparted to said wooden member and generating a signal in response thereto;
   analyzing means for receiving said signal and performing an analysis thereon to determine the intensity as a function of time of said signal, said analyzing means further determining successive time durations required for said intensity to decay to one-half the level previously reached; and
   display means responsive to said time durations from said analyzing means to provide a visual indication representative of the condition of said wooden member.

7. A testing apparatus as set forth in claim 6 wherein said analyzing means includes means for developing said intensity as a function of time from the peak values of said signal.

8. A testing apparatus as set forth in claim 7 wherein said analyzing means operates to determine successive half lives of said intensity as a function of time.

9. A testing apparatus as set forth in claim 6 wherein a first time duration required for said intensity to decay to half its value at the beginning of said first time duration is indicative of the condition of said wooden member and a second time duraction required for said intensity to decay to half its value at the beginning of said second time duration provides a verification of said indication.

* * * * *